United States Patent [19]

Bourinbaiar

[11] Patent Number: 5,541,212

[45] Date of Patent: Jul. 30, 1996

[54] USE OF CIMETIDINE FOR THE CONTROL OF RETROVIRUS INFECTIONS

[75] Inventor: Aldar S. Bourinbaiar, New York, N.Y.

[73] Assignee: Metatron, Inc., Deer Park, N.Y.

[21] Appl. No.: 230,064

[22] Filed: Apr. 21, 1994

Related U.S. Application Data

[63] Continuation-in-part of Ser. No. 179,097, Jan. 10, 1994, abandoned.

[51] Int. Cl.$^6$ .................................................. A61K 31/415
[52] U.S. Cl. .................................................................. 514/400
[58] Field of Search ............................................. 514/400

[56] References Cited

U.S. PATENT DOCUMENTS 5,102,902  4/1992  Mercer ..................................... 514/400
5,286,852  2/1994  Osther .................................. 530/388.35

OTHER PUBLICATIONS

J. Virological Methods, 35, pp. 49–58 (1991).
Immunol. & Infec. Dis., 2, 245–247 (1992).
FEBS Lett., vol. 302, No. 3, 206–208 1992.
E. J. of Pharmacol, 230, (1993) 15–22.
FEBS Lett., vol. 309, No. 1, 82–84 (1992).
Science, vol. 259, 1749–1754 (1993).
J. Inf. Diseases, 167, 1498–9 (1993).
J. of Virology, 67, 2182–2190 (1993).
Science, 229 563–566 (1985).
Science, 260, 1286–1293 (1993).
Virology, 189, 695–714 (1992).
Acta, Virol, 37:241–250 (1993).
Viral Quantitation in HIV Infection, J. M. Andriew, Ed. John Libbey, pp. 41–52 (1992).
Aids Res. & Human Retroviruses, vol. 8, No. 9, p. 1545 (1992).
Clin. Immol, Immunopath. 48, 50–60 (1988).
J. Nat. Cancer Inst., vol. 83, No. 2, 139–141 (1991).
J. Acq. Immuno. Def. Syndromes, vol. 4, No. 6, 577–584 (1991).

*Primary Examiner*—Allen J. Robinson
*Assistant Examiner*—Mary C. Cebulak
*Attorney, Agent, or Firm*—Hedman, Gibson & Costigan, P.C.

[57] ABSTRACT

The invention relates to histamine H2-receptor antagonists such as cimetidine and related compounds such as ranitidine and famotidine that can be used for controlling human immunodeficiency virus (HIV) infection. The preferred agent is cimetidine. The invention comprises a method in vitro as well as in vivo for controlling, i.e., prevention and/or treatment, of HIV infection, associated with the development of acquired immune deficiency syndrome (AIDS), at pharmacological doses of these drugs commonly used for the treatment of gastrointestinal ulcers. The method is based on inhibiting HIV in vitro or on the administration to a host that has been exposed to HIV prior to diagnosis or has been diagnosed as having an HIV infection, of an amount of a H2 antagonist which is sufficient to exert an anti-HIV effect for a sufficient period of time.

4 Claims, 5 Drawing Sheets

USE OF CIMETIDINE FOR THE CONTROL OF RETROVIRUS INFECTIONS

This application is a continuation in part of application Ser. No. 08/179,097, filed Jan. 10, 1994, now abandoned.

FIELD OF THE INVENTION

The present invention relates to the field of chemotherapeutic treatment of viral infections and is particularly directed to a method of treating retroviral infection and infection-associated diseases. This invention relates to histamine type 2 anti-ulcer drugs, and more particularly to cimetidine, ranitidine, and famotidine which are useful for treating diseases caused by retroviral infection and, therefore, the compounds as such and their chemical synthesis are not the part of the present invention.

BACKGROUND OF THE INVENTION

A group of viruses known as retroviruses are of particular concern because they cause diseases that are potentially lethal to an infected host. Retroviruses are a subgroup of RNA viruses that replicate by a reverse transcription mechanism using DNA polymerase that converts viral RNA into proviral DNA which becomes a part of the host cell DNA.

At the present time, several retroviruses are recognized as causative agents of infections in humans and animals. For example, human T cell lymphotropic viruses of type 1 and 2 (HTLV-1 and (HTLV-2) are known as the causative agents of T cell leukemia and debilitating neurological diseases.

The human immunodeficiency virus (HIV-1 & HIV-2) has been recognized as the causative agent of acquired immunodeficiency syndrome (AIDS) and AIDS related complex (ARC). Primary targets of these retroviruses called hereafter by a collective name HIV are believed to be T lymphocytes, responsible for the immune defense, although practically all of the human tissues and cell types can be susceptible to retroviral infection. Retroviral infection causes the disfunction of the immune system. As a result infected individuals may die from opportunistic infections such as pneumonia or from cancers which may be caused directly or indirectly by HIV infection. The final stage of retrovirus-associated malaise is AIDS that currently affects 14 million individuals all over the world. At the present time, most of the treatment for HIV patients is directed to the opportunistic infections or cancers that tend to occur as a infected person's T-cell count is reduced.

Currently available therapy that is directed against retroviruses is based primarily on the use of nucleoside analogues such as azidothymidine (AZT) that interfere with reverse transcription. AZT and other nucleoside analogues have been used in the treatment of AIDS and ARC. However, recent studies have shown that such drugs are inefficient and potentially harmful. Severe toxicity and eventual emergence of resistant viral strains is a major problem associated with the use of these drugs. In addition, long-term therapy with AZT was associated with increased incidence of malignant lymphomas.

In the prior art, cimetidine, ranitidine and famotidine were used as anti-ulcer drugs and their effect in suppressing gastric acid release is commonly associated with their property as an antagonist of histamine type 2 (H2) receptor. Compounds which are H2 antagonists were developed originally as substituted histamines. Cimetidine and related H2 antagonists are also believed to be involved in the modulation of immunity by acting either as inhibitors or enhancers of certain types of immune response. For this reason cimetidine was used in the immunotherapy of cancer in combination with other agents.

The present inventor has discovered that compounds that are antagonists of H2 receptors are useful in vitro as anti-HIV agents because they have a direct antiviral effect. The antagonists of H2 receptors can be also useful in vivo in the treatment of HIV infection. The most common commercially available forms of H2 antagonists are cimetidine, ranitidine and famotidine. There are no known reports in the scientific literature demonstrating specifically the direct antiviral effect of H2 antagonists.

Accordingly it is a primary object of this invention to provide a method for the inhibition of HIV in vitro.

It is also an object of this invention to provide a method for the prevention of the clinical manifestations of the symptoms of HIV infection in a host that has been exposed to HIV.

It is also an object of this invention to provide a method for the treatment of a host that is infected by HIV which involves lifelong therapy to suppress the in vivo replication of HIV. Preferably treatment should commence as soon as an exposure to HIV has been identified or at least prior the manifestation of clinical symptoms of HIV infection.

These and other objects of the invention will become apparent from a review of the appended specification.

SUMMARY OF THE INVENTION

The present invention includes a method for treating and/or preventing HIV infection by administering therapeutically effective doses of the drug of the invention for a sufficient period of time.

The evidence for anti-HIV action of cimetidine and related compounds such as ranitidine and famotidine is provided. The pharmacological doses of cimetidine corresponding to the blood plasma levels of the drug after administration of a 200 mg oral dose prevented de novo HIV infection. The 10 µM concentration of cimetidine completely abolished viral replication without being toxic at the highest tested 1 mM dose. When the term "M" is used herein, it is to be understood that it means moles per liter. A similar, but significantly weaker effect was observed with two other H2 antagonists, ranitidine and famotidine. In contrast, AZT, that was antivirally effective at the similar concentration as cimetidine, was toxic in a dose-dependent fashion to host T lymphocytes. Remarkably, cimetidine was displaying an anti-HIV effect when it was added 18 hours after infection has occurred. This effect was not observed with AZT—the first anti-AIDS drug approved by Food and Drug Administration. Cimetidine was also inhibitory toward related retrovirus HTLV-1. No significant effect was observed when H1 antagonists, diphenhydramine and cyproheptadine, were tested for the activity against HIV infection.

The major elements of the invention can be summarized as follows: (1) Cimetidine appears to be as efficient as AZT; (2) In contrast to AZT, cimetidine is not toxic; (3) In contrast to AZT, cimetidine is efficient in suppressing viral replication in already infected cells; (4) Cimetidine is more efficient than two other tested H2 antagonists, i.e. , ranitidine and famotidine; and (5) H2 antagonist, cimetidine, but not H1 antagonists can prevent HIV infection.

The preferred embodiment of the drug of the invention is disclosed herein as Formula I.

DETAILED DESCRIPTION OF THE INVENTION

Figure 1:
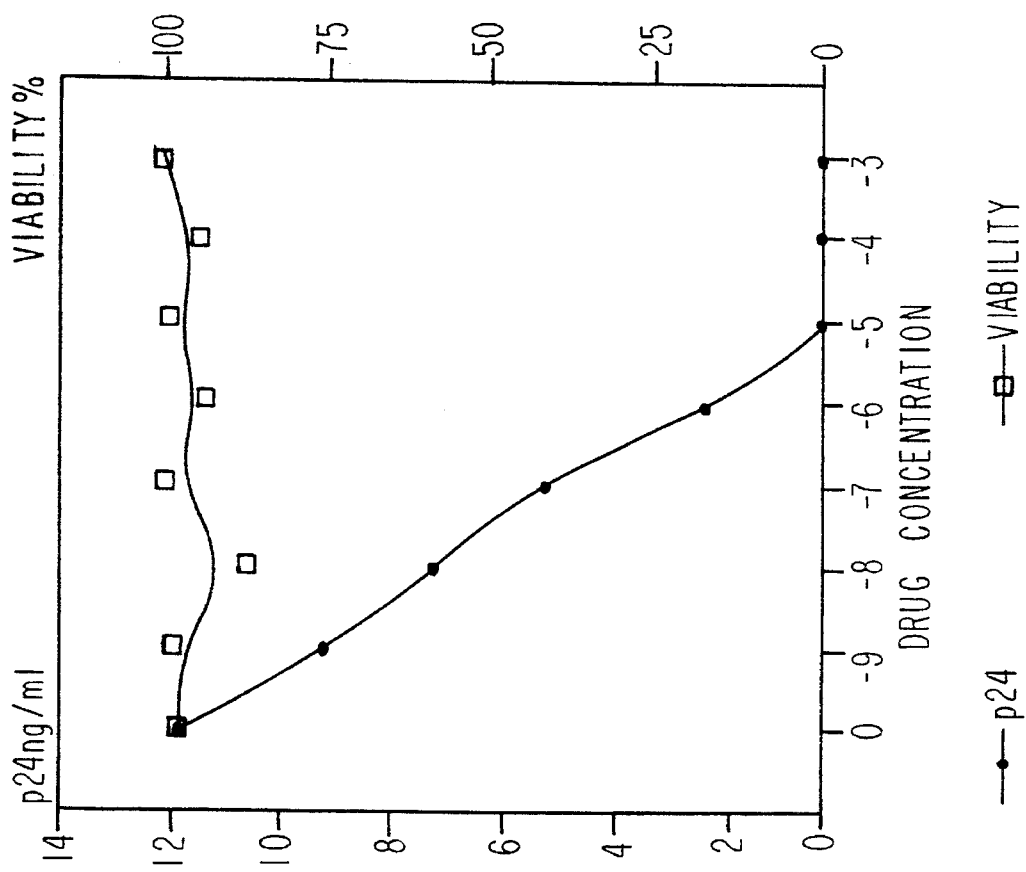
FIG. 1 shows the effect of cimetidine on HIV and viability of MT-4 lymphocytes.

The invention comprises a method for the inhibition of HIV in vitro as well as the prevention and/or treatment of HIV infections in vivo. The method is based on contacting HIV in vitro or on the administration to a host that has been exposed to HIV or has been diagnosed as having an HIV infection, of an amount of an H2 antagonist which is sufficient to exert an anti-HIV effect and continuing the administration of the H2 antagonist for an indefinite period of time. The period of time is that which is sufficient to exert an anti-HIV effect to prevent the exacerbation of the symptoms of the HIV infection. The invention, as applied to the treatment of patients is based on the maintenance of continuous therapeutic blood levels of an H2 antagonist which will inhibit HIV replication and lifelong therapy is contemplated. It is believed that if therapy is discontinued or interrupted, the HIV infection will continue its usual clinical course. Thus, it is contemplated that treatment should preferably start as early as possible following the exposure to HIV. In the treatment of a patient who has been diagnosed as having an HIV infection, it is preferred that treatment be instituted in asymptomatic patients prior to the emergence of any manifestation of the clinical symptoms of ARC or AIDS. Pharmacological doses of cimetidine may be safely administered orally and parenterally. The novel use of cimetidine will be based on currently available oral formulations with various taste masking and sustained release coatings used for the treatment of gastrointestinal disorders, such as peptic ulcer disease and non-ulcer dyspepsia, although it cannot be excluded that specifically devised for antiviral purpose pharmaceutical formulations based on cimetidine or related H2 antagonists will be available in the future. Other H2 antagonists include etintidine, nizatidine and roxatidine as listed in the review article by Lin, Clin. Pharmakin. 20:218–36, 1991, which is incorporated by reference. However, cimetidine is the preferred agent for use in this invention because it is the most effective against HIV and it is readily available at reasonable coast.

The invention also contemplates the use of H2 antagonists in combination with or as an as an adjunct to the use of established anti-AIDS drugs such as AZT (3'-azidothymidine), DDI (2',3'-dideoxyinosine and DDC (2',3'-dideoxycytidine) which are administered at conventional doses. Combination therapy with other anti-AIDS drugs that are useful for treating HIV infection comprising those that are listed in the review article by Johnston & Hoth, Science 260:1286–93, 1993, which is incorporated by reference.

Cimetidine (N-Cyano-N'-methyl- [2-[[5-methyl-1H-imidazol-4-yl)methyl]thio]ethyl]guanidine), ranitidine (N-[2-[[ [-5[( Dimethylamino )methyl]-2-furanyl]methyl]thio]ethyl] -N'-methyl- 2-nitro-1,1ethene-diamine), and famotidine 3-[ [[2-Aminoiminomethyl)amino]- 4-thiazolyl]methyl]thio]- N-(aminosulfonyl)propanimidamide were synthesized previously as described in U.S. Pat. Nos. 3,950,333, 4,128, 658, and 4,283,408 respectively, which are incorporated by reference. Therefore the compounds as such and their chemical synthesis are not part of the present invention. Substituted histamine compounds which are H2 antagonists are well known in the art.

The present invention includes the use of compounds of Formula I:

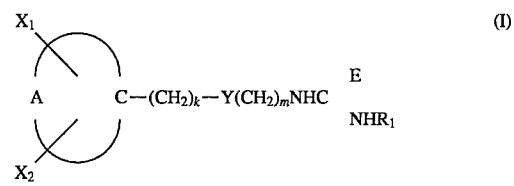

wherein A is such that there is formed together with the carbon atom shown an unsaturated heterocyclic nucleus, said unsaturated heterocyclic nucleus being an imidazole, pyrazole, pyrimidine, pyrazine, pyridazine, furan, thiazolyl or indole ring; $X^1$ is hydrogen, lower alkyl, hydroxy, trifluoromethyl, benzyl, halogen, amino or

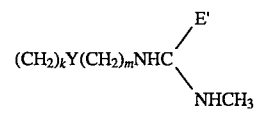

in which E' is NH or N-cyano; $X_2$ is hydrogen or when $X_1$ is lower alkyl, lower alkyl or halogen; k is 0 to 2 and m is 2 or 3 provided that the sum of k and m is 3 or 4; Y is sulfur or oxygen of NH; E is $NR_2$; $R_1$ is hydrogen, lower alkyl or di-lower alkyl amino-lower alkyl; and $R_2$ is hydrogen, nitro or cyano, or a pharmaceutically acceptable addition salt thereof with the proviso that $X_1$ is

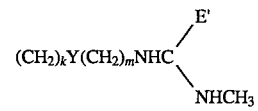

only when E is NH or N-cyano. A preferred compound is N-cyano-N'- methyl-N''-[2-[[(5-methyl-1H-imidazol-4-yl) methyl]thio]ethyl] guanidine which is commercially available as cimetidine. The structural formula of cimetidine is as follows.

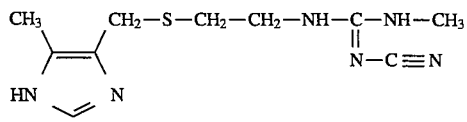

The H2 antagonist may be used in vitro to inhibit HIV in cell cultures by adding from 0.024 μg to 240 μg of H2 antagonist per ml of cell culture. The H2 antagonist may be used to treat HIV infection and/or prevent the emergence of the clinical symptoms of the infection in mammals and humans by administering a sufficient amount of H2 antagonist to provide a continuous blood level of from about $10^{-7}$ to $10^{-4}$M of H2 antagonist. The drug may be administered orally or as a bolus, or parenterally and a dose from 200 mg up to 2000 mg per day will be given in 3 to 4 divided portions. The preferred method of the invention contemplates the administration of the drug orally on a continuous basis throughout the life of the patient. Those who are skilled in the art may adjust the dose based on the response which may be monitored by immunological and virological testing during the course of therapy. The $ICs_{50}$ for cimetidine is about 0.01 µg/ml of serum and that this level may easily be obtained in a 70 kg human by an oral dose of 200 mg of cimetidine (which is commercially available as Tagamet) administered orally every 6 to 8 hours and this dose may be employed for the treatment of HIV infections in mammals and humans. The invention also includes a method of treating an HIV infection which comprises administering to a host which is infected with HIV, an effective amount of an H2 antagonist in combination with an anti-vital treatment such as AZT, DDI or DDC for a sufficient period of time to inhibit HIV.

The invention also includes a pharmaceutical composition which comprises an H2 antagonist and an anti viral drug such as AZT, DDI and DDC.

The anti-HIV action of the H2 antagonists was demonstrated by testing particular compounds in vitro against HIV infected MT-4 lymphocytes. The following test procedure was employed:

EXAMPLE

In a classical virology assay aimed at testing the antiviral activity of a drug the virus is added in the presence of a drug to target cells for the determined period of inoculation time, e.g., 1 hour and then nonadsorbed virus is washed away and inoculated cells are exposed again to a fresh drug. After several days, a period corresponding to the replication cycle of the virus, the dose-effect of the drug is tested by measuring the quantity of newly-synthesized virus in the culture supernates of inoculated cells. In the past, this approach was used, Bourinbaiar et al., Acta Virol. 37:241–50, 1993, but it has been realized that this strategy is not truly representative of the in vivo situation. It is clear that in a real-life situation the virus is not "flushed" from a human body prior to drug administration. Contrary, the "mixture" of the pathogen, drug, and target cells or tissues ought to be present in a continuous manner in a human body until the drug is metabolized. In the present assay virus, drug and cells were left without washing in the culture until tested for virus production 3 days later. This period of time represents one full cycle of HIV replication, Dimitrov et al., J. Virol. 67:2182–90, 1993. It is believed that this type of approach represents more closely the situation in vivo.

The MT-4 cell line used in the present example is the lymphocytic T cell line commonly used in antiviral assays for testing the effect of experimental drugs against HIV infection and is described in Harada et al., Science 229:563–6, 1985. These cells were seeded in 96-well microculture plates ($2\times10^4$ cells/well or $10^5$ cells/ml) containing serial ten-fold dilutions of cimetidine ($10^{-3}$–$10^{-9}$M). Immediately thereafter, $10^2$ vital particles per lymphocyte or an equivalent of 1 ng/ml of p24 gag product of HIV-1 were added per well. The viral stock used in the infection assay was derived from the culture supernatant of H9 lymphocytes carrying IIIB strain and was equal to 10 ng/ml p24. 20 µl of this preparation was added to 180 µl of culture medium containing target lymphocytes and serial dilutions of experimental drugs. The determination of the infectious doses of HIV was based on the concentration of p24 in relation to the molecular weight of HIV particle and the ratio of infectious to defective particles carried out as described earlier: Bourinbaiar, Nature 349:111, 1991; Bourinbaiar, AIDS Res Human Retrovir., 8:1545, 1992; Bourinbaiar et al., In: Viral Quantitation in HIV Infection, (J. M. Andrieu, ed), John Libbey Eurotext, Paris, pp. 41–52, 1991. The correctness of these calculations has been confirmed by other investigators who arrived to these conclusions independently: Lu & Andrieu, J. Infect. Dis. 167:1498–9, 993; Piatak et al., Science 259:1749–54, 1993.

The inoculated MT-4 cells were cultured without washing for 3 days in 200 µl of RPMI 1640 medium (DIFCO) with 10% fetal calf serum in an incubator with 5% $CO_2$ containing humidified air. Two types of controls were used in this test. Positive and negative controls were grown in similar conditions and consisted of cells that were either exposed to virus or were not exposed to virus. AZT was used as a positive drug control at the same molar concentrations as the other drugs. H1 antagonists, diphenhydramine and cyproheptadine, were also tested at the same molar amounts to compare their effect to H2 antagonists.

Three days later, the supernates of infected MT-4 cultures were collected and diluted 10-fold by adding 20 µl of the viral media into ELISA wells containing 160 µl of RPMI1640/10%FCS and 20 µl of lysing buffer. The reliable detection range of the commercially available p24 ELISA kit (Coulter, Hialeah. Fla.), used in our study, is between 10 ng/ml and 10 pg/ml of p24. In order to fit into that range the samples of vital supernatants were titrated in preliminary studies and then p24 measurements were routinely carried out with samples that were diluted ten-fold. The dose effect of the tested drugs was determined by use of the following technique: detergent-lysed samples of culture medium that were incubated in wells (96-well format) precoated with anti-p24 antibody and were screened for gag antigen by adding biotin-labeled anti-p24 antibody followed by streptavidine-peroxidase conjugate. The amount of captured p24 was measured by comparing the optical density (at wavelength 470 nm) of peroxidase substrate, tetramethylbenzidine, with supplied standards containing known amounts of p24. The amount of original vital inoculum (equivalent of 1 ng/ml of p24) left for 3 days in 200 µl volume of medium without lymphocytes was read as a "blank" well and has been subtracted from experimental values. This procedure resolves the problem of discriminating the "left-over" input virus from newly synthesized virus. This rationale is based on our own observations and studies by others: Lu & Andrieu, J. Infect. Dis. 167:1498–9, 1993; Layne et al., Virology 189:695–714, 1992 showing that although infectious activity of virus left in a culture medium may decline rapidly, the p24 antigen does not decay within the first 100 hours of culture. Thus, the amount of residual p24 detected by ELISA in a "blank" well remains equivalent to 1 ng/ml. This value was reproducible at each assay and was subtracted as a "blank" from the readings of experimental wells.

The cytotoxic effect of the exposure to H2 antagonists and control drugs was tested at the same time using $^3H$ thymidine uptake and a colorimetric tetrazolium dye reduction (XTT, Sigma) assay as described by others, Roehm et al., J. Immunol. Methods 142:257–65, 1991.

Based on six separate experiments with 3 replicates for each concentration of drug it can be concluded the effect of cimetidine in inhibiting HIV infection is consistent and reproducible. Typically, the 50% reduction in vital infectivity ($IC_{50}$) was observed at as low as $4.66\times10^{-8}$M or equivalent of 0.01 µg/ml of cimetidine. The complete inhibition of viral infection was observed at $10^{-5}$M or 2.4 µg/ml. At the same time even the highest millimolar dose ($10^3$M or 240 µg/ml) of the drug has not shown any appreciable cytotoxicity (FIG. 1). The $IC_{50}$ dose is 100-fold lower of the peak blood levels of cimetidine (i.e., 1 µg/ml) after administration of a standard 200 mg oral dose. The serum concentrations of cimetidine that are responsible for 50% reduction of gastric acid secretion are equal to 0.5–1 µg/ml. This concentration of drug can persist for up to 6–8 hours after oral uptake of a standard dose of cimetidine in accordance with Bodemar et al., In: Cimetidine (W. Creutzfeldt, ed), Excerpta Medica, Amsterdam-Oxford, pp. 229–32, 1977. The slow plasma clearance of cimetidine indicates that dosing could be infrequent and still maintain effective, therapeutic tissue concentrations.

FIG. 1 is a graph which shows the inhibitory effect of cimetidine on viral production as a decline in the level of gag antigen p24 (expressed in ng/ml on the left abscissa) and the effect of cimetidine on the viability of MT-4 lymphocytes (expressed as a percent of control untreated cells on the right abscissa) after three days of continuous exposure to the drug. These data show that there is essentially no cytotoxicity which can be attributed to concentrations of cimetidine of from $10^{-9}$ to $10^{-3}$M. It is concluded from the data of FIG. 1 that a 50% reduction in viral particles ($IC_{50}$) is seen when a concentration of $10^{-7}$M of cimetidine is present. A 100% reduction in viral production is seen when a concentration of $10^{-5}$ to $10^{-3}$M of cimetidine is used.

Figure 2:
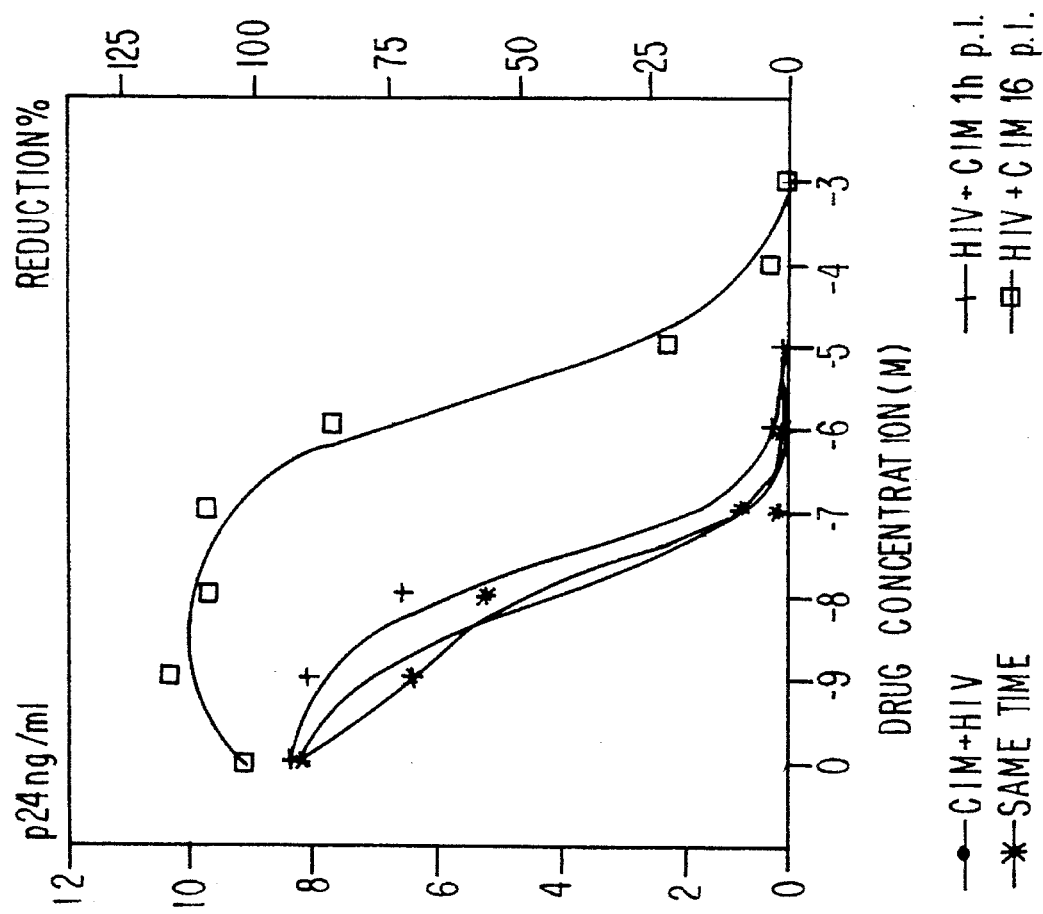
FIG. 2 shows the effect of cimetidine on HIV depending on the time when the culture is inoculated with HIV.

FIG. 2 shows the effect of the simultaneous exposure to HIV and cimetidine as well as the effect of the addition of cimetidine 1 hour before, 1 hour after and 16 hours after inoculation of the culture with HIV. No significant difference is observed when cimetidine was added either 1 hour before, 1 hour after, or simultaneously with the virus. In addition, cimetidine, when added 16 hours postinfection, suppressed completely the vital replication in already infected cells at concentration equal $10^{-4}$M or 24 µg/ml.

Figure 3B:
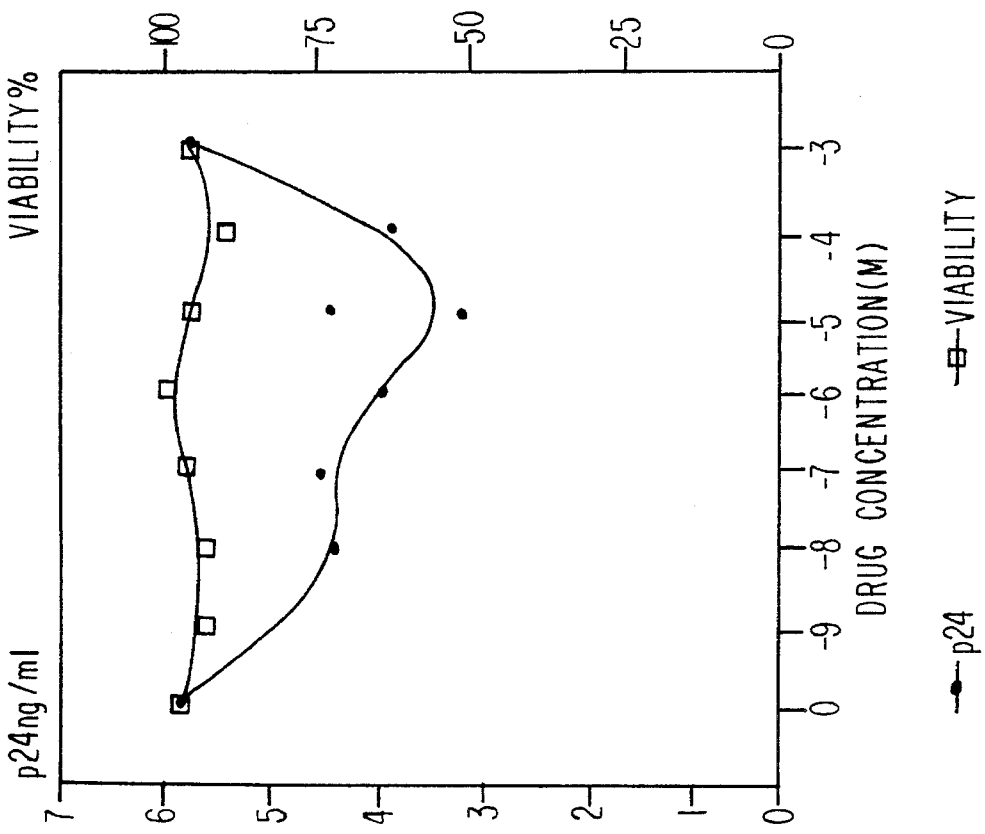
FIG. 3b shows the effect of famotidine on de novo HIV infection and viability of MT-4 lymphocytes.
Figure 3A:
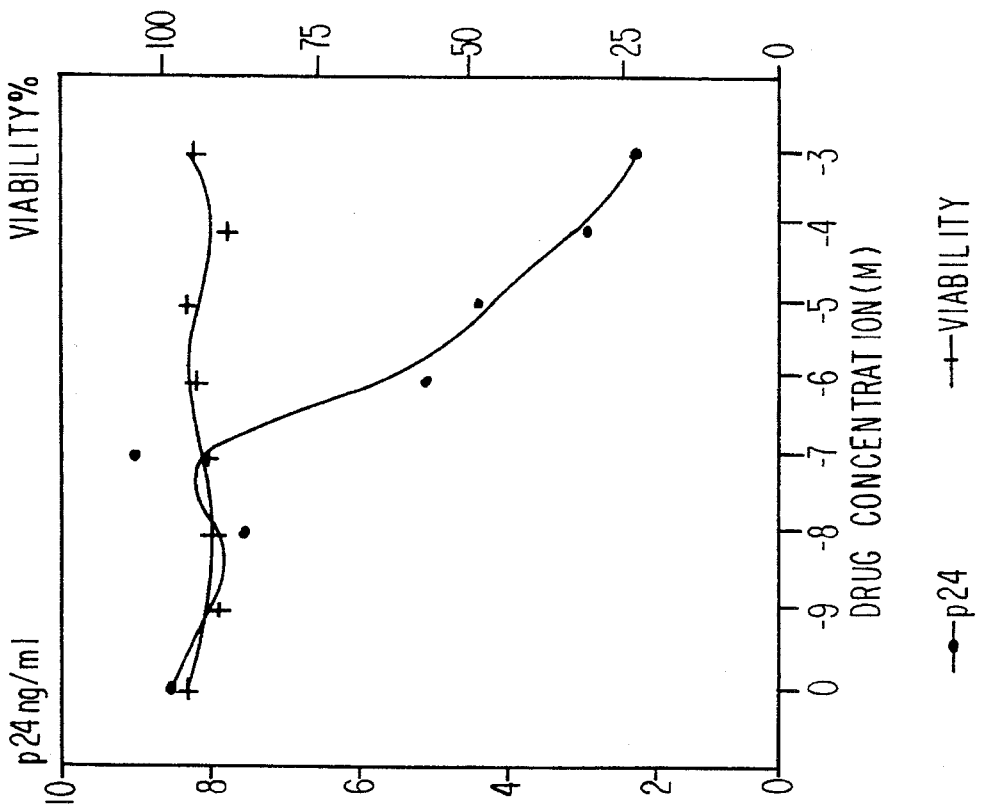
FIG. 3a shows the effect of ranitidine on de novo HIV infection and viability of MT-4 lymphocytes.

The effect of ranitidine and famotidine on HIV infection and cell viability is shown in FIGS. 3a & 3b. Although, a limited antiviral effect was observed with both drugs, no 100% inhibition of vital production was observed at any time even at the highest tested $10^3$M dose.

Figure 4:
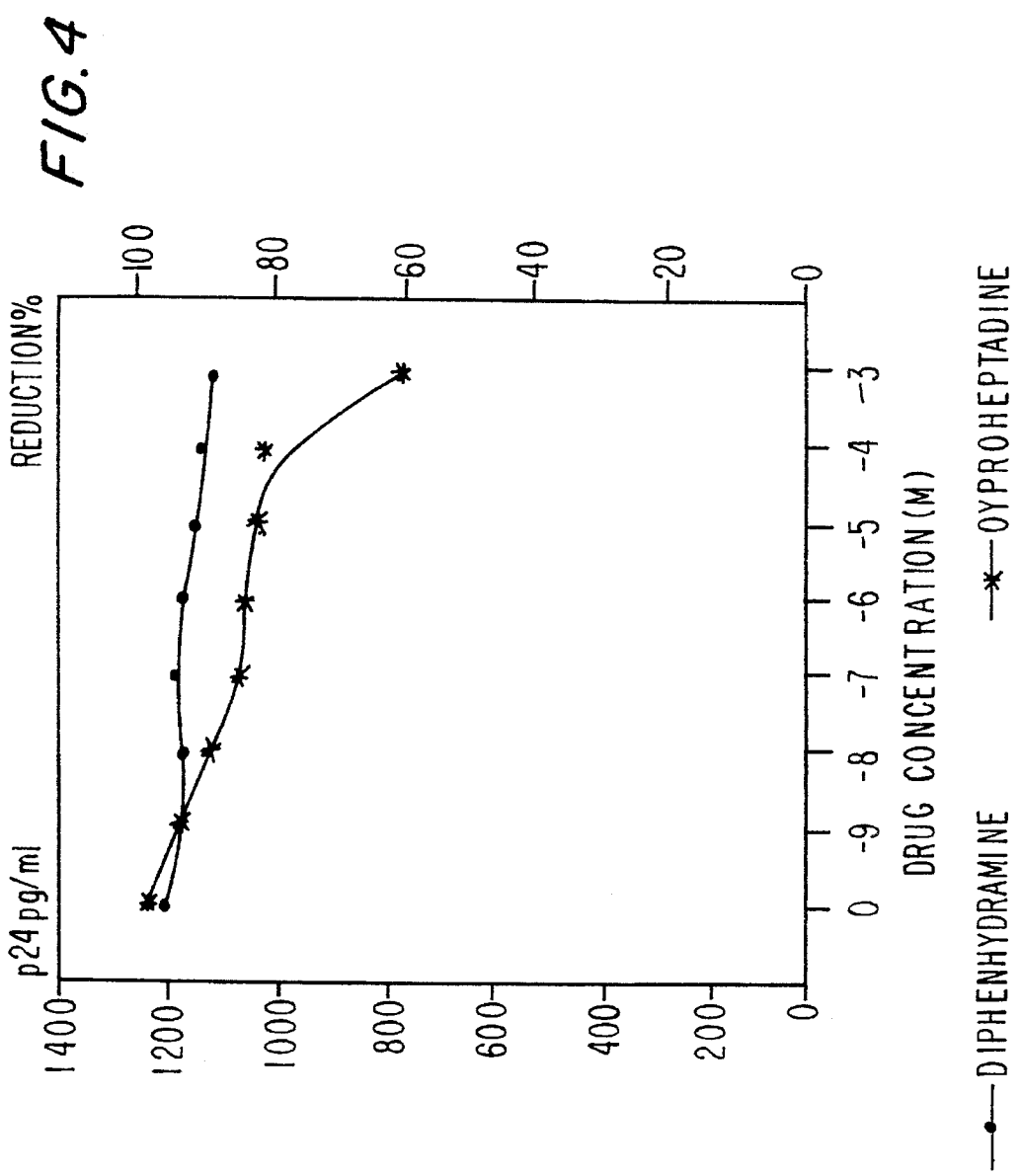
FIG. 4 shows comparative data regarding the effect of H1 antagonists, diphenhydramine and cyproheptadine, on HIV infection.

FIG. 4 provides comparative data regarding the effect of the H1 antagonists, diphenhydramine and cyproheptadine, on HIV. Except for the highest tested millimolar doses H1 antagonists had no significant effect on HIV infection.

Figure 5:
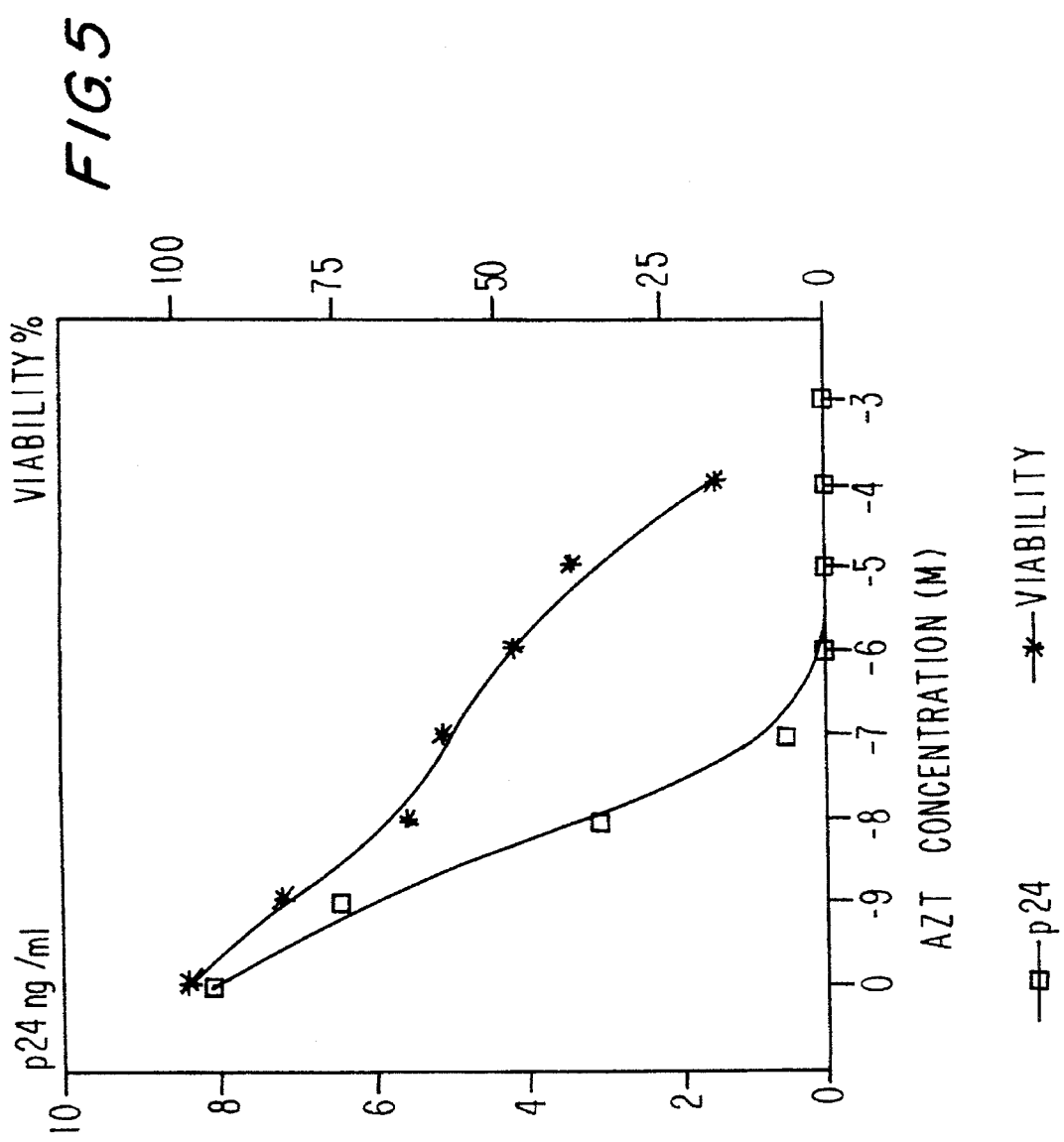
FIG. 5 shows the effect of AZT on HIV and cytotoxic effect of AZT.

FIG. 5 provides comparative drug data which shows the inhibitory effect of AZT on HIV and the cytotoxic effect of AZT. These data suggest that the use of cimetidine as a therapeutic agent is less toxic and, thus, more effective than therapy with AZT.

Although the present invention has been described in some detail for the purposes of clarity and understanding, it will be obvious to those skilled in the art that certain changes and modifications may be practiced within the scope of the appended claims.

What is claimed is:

1. A method for the suppression of the in vivo replication of HIV which comprises administering to a patient infected with HIV who has not exhibited clinical symptoms of an HIV infection an amount of cimetidine which is sufficient to exert an anti-HIV effect for a sufficient period of time to prevent the emergence of clinical symptoms of HIV infection.

2. A method as defined in claim 1 wherein said method comprises administering 200 mg/day to 2,000 mg/day of cimetidine.

3. A method for the suppression of the in vivo replication of HIV which comprises administering to a host which is infected with HIV but is asymptomatic, an effective amount of cimetidine in combination with an anti-vital treatment for a sufficient period of time to suppress the in vivo replication of HIV.

4. A method for the suppression of the in vivo replication of HIV as defined in claim 3 which comprises administering to a host which is infected with HIV but is asymptomatic, an effective amount of an H2 antagonist in combination with an anti-vital drug selected from the group consisting of 3'-azidothymidine, 2',3'-dideoxyinosine and 2',3'-dideoxycytidine.

* * * * *